United States Patent [19]
Osuna, Jr. et al.

[11] Patent Number: 5,714,086
[45] Date of Patent: Feb. 3, 1998

[54] PROPARGYL ETHER-CONTAINING COMPOSITIONS USEFUL FOR UNDERFILL APPLICATIONS

[75] Inventors: Jose A. Osuna, Jr.; Stephen M. Dershem, both of San Diego, Calif.

[73] Assignee: Quantum Materials, Inc., San Diego, Calif.

[21] Appl. No.: 694,903

[22] Filed: Aug. 9, 1996

[51] Int. Cl.$^6$ .................................................. C09K 3/00
[52] U.S. Cl. ................................ 252/182.18; 437/211
[58] Field of Search .................. 252/182.18; 525/328.1; 526/262, 263; 528/205; 568/640; 437/211, 212

[56] References Cited

U.S. PATENT DOCUMENTS

| | | | |
|---|---|---|---|
| 4,885,403 | 12/1989 | Inbasekaran et al. | 568/631 |
| 4,916,203 | 4/1990 | Pigneri et al. | 528/101 |
| 4,946,928 | 8/1990 | Jackson et al. | 528/205 |
| 4,965,331 | 10/1990 | Jackson et al. | 526/262 |
| 4,987,272 | 1/1991 | Pigneri | 568/640 |
| 5,204,415 | 4/1993 | Pigneri | 525/328.1 |
| 5,292,688 | 3/1994 | Hsiao et al. | 437/209 |
| 5,340,931 | 8/1994 | Yamada et al. | 534/843 |

FOREIGN PATENT DOCUMENTS

| | | |
|---|---|---|
| 0369527 A2 | 5/1990 | European Pat. Off. . |
| 0410547 A2 | 1/1991 | European Pat. Off. . |

OTHER PUBLICATIONS

A. S. Hay, D. A. Bolton, K. R. Leimer, R. F. Clark, Polymer Letters, vol. 8, pp. 97–99 (Jan. 1970).

S. Oh, R. Ezaki, K. Akagi, H. Shirakawa, Journal of Polymer Science (a): Polymer Chemistry, vol. 31, 2977–2985 (Aug. 1993).

I. Tomita, J. Lee, T. Endo, Macromolecules vol. 28, 5688–5690 (1995).

Douglas and Overend, "Catalysis of crosslinking of an ethynylaryl–terminated monomer." *Polymer Communications*, 32(16):495–496 (1991).

Douglas and Overend, "Curing Reactions in Acetylene Terminated Resing–I. Uncatalyzed Cure of Arypropargyl Ether Terminated Monomers." *Eur. Polym. J.*, 27(11):1279–1287 (1991).

Douglas and Overend, "Curing Reactions in Acetylene Terminated Resins–III. DSC, TGA and TMA Study of Catalyzed Cure of an Ethynylaryl–Terminated Monomer." *Eur. Polym. J.*, 29(11):1513–1519 (1993).

Dirlikov and Feng, "Propargyl Terminated Resins. A New Hydrophobic Thermosetting Material." *3rd International SAMPE Electronics Conference*, 169–177 (1989).

Dirlikov, S.K., "A Review of Propargyl Terminated Resins." *ACS Polymeric Materials Science and Eng.*, 62:603–607 (1990).

Dirlikov, S.K., "Polymers for all seasons." *Chemtech*, pp. 32–37 (Oct. 1993).

Primary Examiner—Charles T. Jordan
Assistant Examiner—John R. Hardee
Attorney, Agent, or Firm—Gray Cary Ware & Freidenrich; Stephen E. Reiter

[57] ABSTRACT

In accordance with the present invention, there are provided novel propargyl ether-based compositions that are very effective when used in underfill applications. Aromatic propargyl ether compounds are believed to represent the most robust resin chemistry currently available to meet the many performance requirements associated with underfill applications. Propargyl ether resins are hydrophobic, hydrolytically stable, low toxicity monomers that can be cured to high $T_g$, thermally stable thermosets. Liquid propargyl ether monomers have been found and/or described in the literature which can be used alone or in combination to yield diluent free underfill compositions. Alternatively, mixtures of two or more propargyl ether monomers (wherein one or more of these monomers may be solids at room temperature) can be used to create diluent-free, room temperature stable, eutectic or peritectic liquid resin compositions. In accordance with the present invention it has furthermore been found that transition metal compounds (in chelated or soap forms) can be used to catalyze the rapid cure of propargyl ether monomers. This cure is especially facile in the presence of additional coordinating ligand additives.

25 Claims, No Drawings

5,714,086

PROPARGYL ETHER-CONTAINING COMPOSITIONS USEFUL FOR UNDERFILL APPLICATIONS

FIELD OF THE INVENTION

The present invention relates to novel compositions and uses therefor. In a particular aspect, the present invention relates to compositions useful for underfill applications, i.e., compositions useful for filling the gap which exists between the supporting substrate and semiconductor device in a flip-chip assembly. In another aspect, the present invention relates to methods for using such compositions.

BACKGROUND OF THE INVENTION

A new trend, known as "flip-chip", has emerged in electronic packaging. This packaging methodology permits the manufacture of high population density electronic devices, while also eliminating the need for wire bonding. The elimination of wire bonds is significant since, as the number of inputs and outputs (I/Os) has increased (as a function of electronic device complexity) so has the potential for "cross-talk" (i.e., radio frequency interference between I/Os). The wire bonds literally act as antennas for this cross-talk phenomenon.

Flip-chip technology involves the direct deposition of a solder bump array onto a microelectronic device. One or more of such "bumped" components can then be directly attached to an electronic assembly via a solder reflow step in which the component is soldered to the device with the microelectronic circuitry face down. Flip-chip technology offers significant gains for high density electronic packaging. It also, however, creates some new manufacturing and reliability problems.

For example, mismatches in thermal expansivity between the microelectronic device and the substrate to which it is attached place severe stress on the solder bump connections. Repeated thermal cycling, such as would occur as the device is powered up and down, can fatigue the solder bump connections and lead to their eventual failure. It is well recognized by those of skill in the art that substantial improvements in fatigue resistance can be obtained by displacement of the interstitial air space between the solder bumps with a high modulus, low coefficient of thermal expansion (CTE) "underfill" resin composition. Presumably, the insertion of the underfill resin composition serves to stiffen the solder bump attachment region and to help this junction resist lateral displacement forces that arise via the CTE mismatch between the device and substrate.

Additional features that resin compositions should have to be useful for underfill applications include low viscosity, high hydrophobicity, a rapid cure schedule, and good homogeneity. Low viscosity is a requirement since the underfill material must rapidly wick into the gap between the microelectronic device and substrate. Hydrophobicity is desirable since the presence of adsorbed moisture in the resin (either in the free volume or in void imperfections) can be released with explosive force during subsequent heating operations such as solder reflow. The explosive release of water during solder reflow is the root cause of a phenomenon termed "popcorning" and is a reliability failure. A further practical requirement for an underfill resin composition is that the process time required to develop its necessary properties should be short. The processing time should not exceed one to two hours, and preferably should be 15 minutes or less at a maximum temperature not to exceed 170° C. (or preferably 150° C.).

A related requirement is that the underfill resin composition should be free of any non-reactive diluent species. It may be necessary to add one or more fillers to the underfill resin composition. These fillers can be used to reduce the CTE of the cured resin composition. It is furthermore desirable that these fillers comprise isotropic spherical particles. Spherical filler geometry is preferred since this shape lends itself to a rapid and uniform impregnation of the underfill space. Desirable fillers are also chemically inert, free of significant extractable ions, thermally stable, and posses very low or negative CTE values between −100° to 200° C.

There is still a need in the art for underfill resin compositions which meet or exceed the combination of performance criteria recited above.

BRIEF DESCRIPTION OF THE INVENTION

In accordance with the present invention, we have discovered that propargyl ether-based compositions are very effective when used in underfill applications. Aromatic propargyl ether compounds are believed to represent the most robust resin chemistry currently available to meet the many performance requirements associated with underfill applications. Propargyl ether resins are hydrophobic, hydrolytically stable, low toxicity monomers that can be cured to high $T_g$, thermally stable thermosets.

Liquid propargyl ether monomers have been found and/or described in the literature which can be used alone or in combination to yield diluent free underfill compositions. Alternatively, mixtures of two or more propargyl ether monomers (wherein one or more of these monomers may be solids at room temperature) can be used to create diluent-free, room temperature stable, eutectic or peritectic liquid resin compositions. In accordance with the present invention it has furthermore been found that transition metal compounds (in chelated or soap forms) can be used to catalyze the rapid cure of propargyl ether monomers. This cure is especially facile in the presence of additional coordinating ligand additives.

The ultimate glass transition values that can be attained with low molecular weight aromatic propargyl ether compounds can equal or exceed 300° C. Unfortunately, the cure schedules (i.e. both temperature and time) required to reach these ultimate $T_g$ values exceed those that would be commercially viable for traditional electronic component assembly. In accordance with the present invention, however, it has been found that properly catalyzed propargyl ether compositions can achieve desirable glass transition values within fifteen minutes at temperatures less than or equal to 150° C.

DETAILED DESCRIPTION OF THE INVENTION

In accordance with the present invention, there are provided compositions useful for protecting solder interconnections between semiconductor devices and supporting substrates therefor. Invention compositions comprise:

in the range of about 20 up to 80 wt % of a curable thermosetting propargyl ether-based binder system, wherein said binder system has a viscosity at room temperature of no greater than about 2,500 centipoise, and wherein said binder system comprises:
  in the range of about 50 up to about 5000 parts per million, on a metals basis, of a transition metal curing catalyst, and
  in the range of about 0.1 up to about 10 wt % of an accelerator, based on the total weight of the binder system, and in the range of about 20 up to 80 wt % of a filler having a maximum particle size of about 50 microns.

As employed herein, wt % is based on the total weight of the composition unless otherwise indicated.

Propargyl ether-based binder systems contemplated for use in the practice of the present invention comprise at least one propargyl ether and optionally one or more additional monomers such as, for example, vinyl ethers, divinyl ethers, diallyl ethers, monomaleimides, bismaleimides, and the like, as well as mixtures of any two or more such monomers.

The propargyl ether-based binder systems contemplated for use in the practice of the present invention further comprise a sufficient quantity of a transition metal curing catalyst and an accelerator to promote the rapid curing of the composition when subjected to curing conditions. Typically, the transition metal curing catalyst is present in the range of about 50 up to about 5000 parts per million (on a metals basis), with in the range of about 500 up to about 1500 parts per million being preferred to promote rapid curing of most formulations. Transition metal curing catalysts contemplated for use in the practice of the present invention include nickel, copper, cobalt and the like, in the form of a chelate, a soap, or the like.

Typically, the accelerator is present in the range of about 0.1 up to about 10 wt %, based on the total weight of the binder system, with in the range of about 3 up to about 5 wt % being preferred. Accelerators contemplated for use in the practice of the present invention include phosphines, phosphites, tertiary amines, and the like, as well as Lewis acid complexes thereof.

Presently preferred compositions according to the invention comprise in the range of about 25 up to about 50 wt % of the curable thermosetting propargyl ether-based binder system, and in the range of about 50 up to about 75 wt % filler.

Optionally, invention compositions can further comprise one or more of the following additional components, e.g., coupling agents, thixotropes, dyes, anti-oxidants, surfactants, inert diluents, reactive diluents, anti-bleed agents, fluxing agents, and the like.

Coupling agents (also referred to herein as adhesion promoters) contemplated for use in the practice of the present invention include silicate esters, metal acrylate salts (e.g., aluminum methacrylate), titanates (e.g., titanium methacryloxyethylacetoacetate triisopropoxide), or compounds that contain a copolymerizable group and a chelating ligand (e.g., phosphine, mercaptan, acetoacetate, and the like). When added to invention compositions, generally in the range of about 0.1 up to 5 wt % of at least one coupling agent (based on the total weight of the organic phase) will be employed, with in the range of about 0.5 up to 2 wt % preferred.

Presently preferred coupling agents contain both a co-polymerizable function (e.g., vinyl moiety, acrylate moiety, methacrylate moiety, styrene moiety, cyclopentadiene moiety, and the like), as well as a silicate ester function. The silicate ester portion of the coupling agent is capable of condensing with metal hydroxides present on the mineral surface of the substrate, while the co-polymerizable function is capable of co-polymerizing with the other reactive components of invention adhesive composition. Especially preferred coupling agents contemplated for use in the practice of the invention are oligomeric silicate coupling agents such as poly(methoxyvinylsiloxane).

Thixotropes contemplated for use in the practice of the present invention include fumed alumina, fumed silica, fumed titanium dioxide, graphite fibrils, teflon powder, organo-modified clays, thermoplastic elastomers, and the like.

Dyes contemplated for use in the practice of the present invention include nigrosine, Orasol blue GN, non-electrically conductive carbon black, and the like. When used, organic dyes in relatively low amounts (i.e., amounts less than about 0.2 wt %) provide contrast.

Anti-oxidants contemplated for use in the practice of the present invention include hindered phenols (e.g., BHT (butylated hydroxytoluene), BHA (butylated hydroxyanisole), TBHQ (tertiary-butyl hydroquinone), 2,2'-methylenebis(6-tertiarybutyl-p-cresol), and the like), hindered amines (e.g., diphenylamine, N,N'-bis(1,4-dimethylpentyl-p-phenylene diamine, N-(4-anilinophenyl) methacrylamide, 4,4'-bis($\alpha,\alpha$-dimethylbenzyl) diphenylamine, and the like), phosphites, and the like.

Surfactants contemplated for use in the practice of the present invention include silanes and non-ionic type surface active agents. Surfactants in amounts of about 0.5 wt % up to about 3 wt % (preferably about 1.2 wt % up to about 1.6 wt % can be used to facilitate mixing the filler with the propargyl ether-based resin system.

While not preferred in the practice of the present invention, it is of course recognized that inert diluents can be employed. When employed, inert diluents contemplated for use in the practice of the present invention include any diluent which is inert to the propargyl ether-based resin compositions described herein, and in which the resin has sufficient solubility to facilitate handling. Representative inert diluents include dimethylformamide, dimethylacetamide, N-methylpyrrolidone, toluene, xylene, methylene chloride, tetrahydrofuran, methyl ethyl ketone, monoalkyl or dialkyl ethers of ethylene glycol, polyethylene glycol, propylene glycol or polypropylene glycol, glycol ethers, and the like.

Reactive diluents contemplated for use in the practice of the present invention include any reactive diluent which, in combination with the propargyl ether-based resins described, herein forms a thermosetting resin composition. Such reactive diluents include acrylates and methacrylates of monofunctional and polyfunctional alcohols, ethylenically unsaturated compounds, styrenic monomers (i.e., ethers derived from the reaction of vinyl benzyl chlorides with mono-, di-, or trifunctional hydroxy compounds), and the like.

Fluxing agents contemplated for use in the practice of the present invention include propargyloxy ethers of hydroxy derivatives of aromatic carboxylic acids (e.g., the propaypyloxy ether of parahydroxy benzoic acid), and the like.

Anti-bleed agents contemplated for use in the practice of the present invention include cationic surfactants, tertiary amines, tertiary phosphines, amphoteric surfactants, polyfunctional compounds, and the like, as well as mixtures of any two or more thereof.

Invention compositions typically have excellent handling properties. For example, the viscosity of invention compositions at room temperature generally fall in the range of about 3,000 up to about 150,000 centipoise, with viscosities at room temperature in the range of about 20,000 up to about 60,000 centipoise being readily attainable.

Even where invention compositions have relatively high viscosities at room temperature, these materials have excellent handling properties at typical working temperatures (in the range of about 70° C. up to about 100° C.). Under such conditions, invention compositions typically have viscosities of no greater than about 3,000 centipoise.

Propargyl ethers contemplated for use in the practice of the present invention can be represented by structure I as follows:

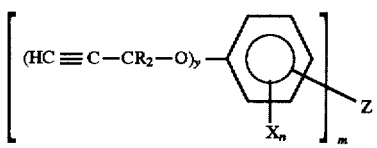

(I)

wherein:
X, when present, is selected from alkyl, cycloalkyl, alkenyl, alkynyl, aryl, alkoxy, halogen or cyano;

Z, when present, is a di- or trivalent radical capable of linking two or three of the propargyl moieties;

each R is independently selected from hydrogen or alkyl having up to 40 carbon atoms;

m is 1, 2 or 3;

n is an integer from 0 up to 3; and y is an integer from 1 up to 3.

As employed herein, the term "alkyl" refers to straight or branched chain alkyl radicals having in the range of about 1 up to 8 carbon atoms, and "lower alkyl" refers to straight or branched chain alkyl radicals having in the range of about 1 up to 4 carbon atoms.

As employed herein, the term "alkenyl" refers to straight or branched chain hydrocarbyl radicals having at least one carbon-carbon double bond, and having in the range of about 2 up to 8 carbon atoms.

As employed herein, the term "alkynyl" refers to straight or branched chain hydrocarbyl radicals having at least one carbon-carbon triple bond, and having in the range of about 2 up to 8 carbon atoms.

As employed herein, the term "alkoxy" refers to an oxygen-bearing alkyl moiety having the structure —OR, wherein R is an alkyl group as defined above.

As employed herein, the term "cycloalkyl" refers to cyclic ring-containing radicals containing in the range of about 3 up to 12 carbon atoms.

As employed herein, the term "aryl" refers to aromatic radicals having in the range of 6 up to 14 carbon atoms.

As employed herein, the term "halogen" refers to fluoride, chloride, bromide or iodide radicals.

When the core aromatic ring of structure I is substituted, presently preferred substituents include alkyl, alkenyl or aryl. While up to 3 substituents can be accomodated by propargyl ethers employed in the practice of the present invention, it is presently preferred that no greater than 2 substituents be present (i.e., n is an integer from 0 up to 2).

When the propargyl ether employed herein is a di- or tri-propargyl material, Z can be selected from a wide variety of linking groups. For example, Z, when present, can be:

—O—,

—C(O)—,

—C(O)—O—,

—O—C(O)—O—,

—S—,

—S(O)$_2$—,

—[CR'$_2$]$_x$—, wherein each R' is independently selected from hydrogen, alkyl, fluoroalkyl, cycloalkyl, fluorocycloalkyl or aryl, and x is an integer falling in the range of 1 up to 20, —[O—(CR'$_2$)$_{x'}$]$_y$—O—, wherein each R' is independently as defined above, x' is an integer falling in the range of 1 up to 6, and y is an integer falling in the range of 1 up to 20, —SiR'$_2$—, wherein each R' is independently as defined above, —SiR'$_2$—[—O—SiR'$_2$—]$_{y'}$—, wherein each R' is independently as defined above, and wherein y' is an integer falling in the range of 1 up to 20, —NR'—, wherein each R' is independently as defined above,

arylene, alkylene-arylene, arylene-alkylene, cycloalkylene, bicycloalkylene, or the like. As employed herein, the term "cycloalkylene" refers to cyclic ring-containing divalent radicals containing in the range of about 3 up to 8 carbon atoms (e.g. cyclohexylene); and "bicycloalkylene" refers to divalent bicyclic radicals.

Presently preferred propargyl ethers are dipropargyl ethers, i.e., those wherein m is 2, and wherein R is selected from hydrogen or methyl.

A presently preferred propargyl ether compound contemplated for use herein is the 4,4'-dipropargyl ether of bisphenol E, i.e., a compound according to structure I wherein:

Z is —CH(CH$_3$)—, each R is hydrogen, m is 2, n is 0, and y is 1.

Another presently preferred propargyl ether compound contemplated for use herein is the tripropargyl ether of triphenol ethane, i.e., a compound according to structure I wherein:

Z is

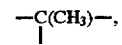

each R is hydrogen, m is 3, n is 0, and y is 1.

Yet another presently preferred propargyl ether compound contemplated for use herein is the dipropargyl ether of 2-phenyl hydroquinone, i.e., a compound according to structure I wherein:

X is phenyl,

Z is not present, each R is hydrogen, m is 0, n is 1, and y is 2.

As readily recognized by those of skill in the art, the above-described propargyl ether compound can similarly be prepared from a derivative of hydroquinone, or from an isomer of hydroquinone (e.g., resorcinol).

Still another presently preferred propargyl ether compound contemplated for use herein is the dipropargyl ether of 4,4'-hexafluoropropylidene diphenol, i.e., a compound according to structure I wherein:

Z is —C(CF$_3$)$_2$—, each R is hydrogen,
m is 2,
n is 0, and
y is 1.

As recognized by those of skill in the art, any one or more of the above-described propargyl-ether-containing binder systems can be subjected to a partial cure (B-stage) prior to preparing the final formulation.

Fillers contemplated for use in the practice of the present invention are preferably substantially spherical, or at least the majority of the filler particles are substantially spherical, so as to facilitate flow of invention composition into the gaps which form between the supporting substrate and the semiconductor device to which it is attached. Fillers suitable for use herein are further characterized as having a low coefficient of thermal expansion, as being substantially non-conductive, and as having low levels of extractable ions. In addition, fillers contemplated for use herein desirably have an emission rate of less than about 0.01 alpha particles/$cm^2$-hr.

Particle sizes of fillers employed in the practice of the present invention are typically 50 microns or less, preferably not greater than about 35 microns and most preferably not greater than about 25 microns. Most preferably at least about 90 weight % of the particles are no smaller than about 0.7 microns. Smaller particle sizes are necessary so that the composite polymer material will readily flow in the gap between the chip and substrate carrier. The gap is normally about 25 to about 50 microns, but in some cases is somewhat larger (e.g., about 75 to about 125 microns). Presently preferred fillers have average particle sizes in the range of about 0.5 up to about 20 micrometers, with particle sizes in the range of about 3 to about 10 microns being especially preferred, even though there may be a distribution of a minor amount of some larger particles.

In addition, according to a preferred aspect of the present invention, the filler is substantially free of alpha particle emissions such as produced from the trace amounts of radioactive impurities (e.g., uranium and thorium) normally present in conventional silica or quartz fillers. The preferred fillers employed in the practice of the present invention have emission rates of less than 0.01 alpha particles/$cm^2$-hr and most preferably less than 0.005 alpha particles/$cm^2$-hr.

The presence of α-particle emissions (primarily caused by the presence of uranium and thorium isotopes in the fillers) can generate electron/hole pairs, which in turn would be detrimental to the device. A presently preferred filler is high purity fused or amorphous silica or synthetic glass commercial fillers which typically are rounded filler particles. A commercially available filler that can be employed is DP4910 from PQ Corporation. The preferred filler can optionally be treated with a coupling agent.

Exemplary fillers contemplated for use herein include alumina, aluminum nitride, boron nitride, borosilicate glass, diamond dust, silica, quartz, silicon, silicon carbide, titania, zirconium tungstate, and the like, optionally treated with coupling agents and/or lubricants.

In accordance with another embodiment of the present invention, there are provided methods of protecting solder interconnections between semiconductor devices and supporting substrates, said method comprising:

attaching said device to said substrate by a plurality of solder connections that extend from the supporting substrate to electrodes on said semiconductor device, thereby forming a gap between said supporting substrate and said semiconductor device, filling said gap with a composition according to the invention, as described herein, and subjecting said composition to curing conditions.

Substrates contemplated for use herein can be based on either organic material, inorganic material, or combinations thereof. For example, organic substrates contemplated for use herein include thermoplastic and thermosetting resins. Typical thermosetting resinous materials include epoxy, phenolic-based materials, polyimides and polyamides. Such materials are usually molded of the resinous material along with a reinforcing agent such as a glass-filled epoxy or phenolic-based material. Examples of some phenolic-type materials include copolymers of phenol, resorcinol, and cresol. Examples of some suitable thermoplastic polymeric materials include fluorinated polymeric materials, polyolefins such as polypropylene, polysulfones, polycarbonates, nitrile rubbers and ABS polymers.

Selection of a particular organic resin will depend in part on the processing temperatures that the substrate will be subjected to during the soldering. For example, fluorinated polymeric materials contemplated for use herein are well-known and include such commercially available polyfluoroalkylene materials as polytetrafluoroethylene, copolymers of tetrafluoroethylene and hexafluoropropylene, copolymers of tetrafluoroethylene and perfluoro-2,2-dimethyl-1,3 dioxide, polytrifluorochloroethylene, copolymers of tetrafluoroethylene with, for example, olefins such as ethylene; copolymers of trifluoromonochloroethylene with for example olefins such as ethylene, polymers of perfluoroalkyl vinyl ether.

Some commercially available fluorinated polymeric materials which are suitable for use in the practice of the present invention include those available under the trade designation TEFLON PTFE (polymers of tetrafluoroethylene), TEFLON FEP (perfluorinated ethylene-propylene copolymers); TEFLON PFA (copolymer of tetrafluoroethylene and perfluoroalkoxy); TEFZEL (copolymer of tetrafluoroethylene and ethylene); HALAR (copolymer of chlorotrifluoroethylene and ethylene); KEL-F (polymer of chlorotrifluoroethylene); HBF-430 (polymer of chlorotrifluoroethylene) and TEFLON AF (copolymer of tetrafluoroethylene and at least 65 mole % of perfluoro-2, 2-dimethyl-1,3 dioxide). The preferred fluorinated polymeric material is polytetrafluoroethylene (e.g., TEFLON). Commercially available fluorocarbon polymers reinforced with fiber glass are available from Rogers Corporation under the trade designation R02800 and R02500.

The polyimides that can be used as substrates in accordance with the present invention include unmodified polyimides, as well as modified polyimides such as polyester imides, polyamide-imide-esters, polyamide-imides, polysiloxane-imides, as well as other mixed polyimides. Such are well-known in the prior art and need not be described in any great detail.

Typical epoxy resins employed in the practice of the present invention include the bisphenol A type resins obtained from bisphenol A and epichlorohydrin, resinous materials obtained by the epoxidation of novolak resins (produced from a phenolic material such as phenol and an aldehyde such as formaldehyde) with epichlorohydrin, polyfunctional epoxy resins such as tetraglycidyl-diaminodiphenyl methane and alicyclic epoxy resins such as bis(3,4-epoxy-6-methyl-cyclohexylmethyl) adipate. The presently most preferred epoxy employed in the practice of the present invention is the bisphenol A type.

The epoxy resinous compositions also can contain accelerating agents and curing agents as are well-known in the art. Examples of suitable curing agents include polyamines, primary, secondary, and tertiary amines, polyamides, polysulfides, urea-phenol-formaldehyde, and acids or anhydrides thereof. In addition, suitable curing agents include Lewis acid catalysts such as $BF_3$ and complexes thereof.

Many of the organic substrates employed in accordance with the present invention contain the resin and a reinforcing fiber such as fiberglass, polyamide fiber mats (e.g., Kevlar), graphite fiber mats, Teflon fiber mats, and the like. Such compositions containing fibers are usually prepared by impregnating the fibers with, for instance, a composition of a suitable polymer. The amount of the polymer composition is usually about 30% to about 70% by weight (with about 50% to about 65% by weight preferred) of the total solids content of the polymer composition of the fiber support.

In the case of epoxy compositions, for example, such can be prepared by combining with the reinforcing fibers, and then curing to the B-stage and cutting to the desired shape, such as a sheet. When sheets are employed, the thickness is usually about 1.5 mils to about 8 mils. Curing to the B-stage is generally achieved by using temperatures of about 80° C. to about 110° C. for about 3 minutes to about 10 minutes.

If desired, the substrate can then be laminated onto other substrates as well as being interposed between the above electrically conductive patterns present in the support layers. The laminating can be carried out by pressing together the desired structure in a preheated laminating press at a predetermined pressure and temperature as, for example, about 200 psi to about 300 psi at about 180° C. The time of the pressing operation is variable depending upon the particular materials employed and the pressure applied. About 1 hour is adequate for the above conditions.

The organic substrates include the desired electrically conductive circuitry on the top and/or bottom surfaces of the substrate and/or on interior planes of the substrate as well known.

Next, in order to connect the electrically conductive patterns on opposing surfaces of the dielectric material, through-holes in the structure can be made. The through-holes can be obtained by drilling or punching operations including mechanical drilling and laser drilling and subsequently plated.

The organic substrates are generally about 3 to about 300 mils thick and more usually about 40 to about 100 mils thick.

Inorganic substrates contemplated for use herein include silicon supports, ceramic supports (e.g., silicon carbide supports, aluminum nitride supports, alumina supports, berylia supports, and the like), sapphire supports, porcelain coated on steel, and the like.

Dispense and flow conditions employed for applying invention compositions are preferably selected such that the composition forms fillets on all four side walls of the chip. Thus, invention compositions can be applied by dispensing through nozzles under pressure of about 15 to about 90 psi and temperatures of about 25° C. to about 90° C. The compositions preferably completely cover the solder bump interconnections.

If desired, the flow of the compositions under the chip can be accelerated by heating for about 2 to about 20 minutes, typically about 15 minutes at about 40° C. to about 90° C.

Also, if desired, the compositions can be pregelled by heating for about 6 to about 60 minutes typically about to about 15 minutes at about 110° C. to about 130° C. and preferably about 6 to about 10 minutes at about 115° C. to about 120° C.

Curing conditions contemplated for use in the practice of the present invention comprise subjecting the composition to a temperature of up to about 170° C. for up to about 2 hours. Preferably, curing will be carried out at a temperature of up to about 150° C. for up to about 1 hour, with curing at temperatures below about 140° C. for up to about 0.5 hour being presently preferred.

In accordance with yet another embodiment of the present invention, there are provided methods of making compositions useful for protecting solder interconnections between semiconductor devices and supporting substrates. As readily recognized by those of skill in the art, the various components of invention compositions can be combined in any order. It is preferred, however, to add curing catalyst and accelerator therefor at different times so that the energy input to mix the combination of ingredients is less likely to prematurely initiate cure. Thus, for example, propargyl ether resin could be combined with catalyst, then filler added, and finally, accelerator introduced. Alternatively, propargyl ether resin could be combined with filler and/or accelerator, then catalyst added last.

The invention will now be described in greater detail by reference to the following non-limiting examples.

EXAMPLE 1

Preparation of 4,4'-Dipropargyl Ether of Bisphenol E

This example illustrates the general procedure used in Example 1 of U.S. Pat. No. 4,885,403 for the preparation of di-propargyl ethers of di-hydric phenols. To a 500 ml triple necked round bottom flask fitted with mechanical stirring, inlet and outlet $N_2$ gas adapters, liquid addition funnel, and a re-circulating heated water bath were added 42.8 grams of 4,4'-ethylidenediphenol (Bisphenol E, 0.2 moles), 200 ml 20% aqueous sodium hydroxide, and 3.25 grams of tetrabutylammonium bromide (0.01 moles). Following mixing, the reaction solution was stirred and $N_2$ purged while equilibrating to 30° C. (water bath temperature). Next, the addition funnel was charged with 40.0 grams of propargyl chloride (0.54 moles) and added drop-wise over a 2 hour period.

The reaction was allowed to stir overnight at 30° C. The next morning, the reaction solution was washed 2× with 200 ml aliquots of $CH_2Cl_2$ followed by washing the combined organic phases with 2×100 ml aliquots of 5% aqueous sodium hydroxide. Next the organic phase was dried over magnesium sulfate. After filtration of solids, the solvent was removed via rotary evaporation. The crude product was purified by dissolution into hot hexane followed by rotary evaporation of the hexane at ambient and reduced (<0.5 torr) pressure. The final product was a light yellow liquid which solidified slowly on standing (m.p. 39° C.). Isolated product yield was greater than 90% with high purity as determined by spectral analysis.

EXAMPLE 2

Preparation of the Tripropargyl Ether of Triphenol Ethane

A 250 ml round bottom flask fitted with a magnetic stirrer, $N_2$ inlet and outlet adapters, liquid addition funnel, and powder funnel was purged with $N_2$. To the reaction flask was added 150 ml of dimethylsulfoxide (DMSO) followed by 23.5 grams of potassium tert-butoxide (0.21 moles). Triphenol ethane (25.0 grams, 0.059 moles) was added to the powder addition funnel, and then introduced into the reaction vessel portion-wise over the next hour. After 2 additional hours, the addition funnel was charged with 15.6 grams of propargyl chloride (0.21 moles), which was then introduced into the reaction vessel drop-wise over the next hour.

After stirring overnight, the reaction solution was diluted with 200 ml of water and extracted with 2×100 ml aliquots of $CH_2Cl_2$. The organic phases were combined and washed 2× with 100 ml aliquots of 5% (wt) aqueous sodium hydroxide, followed by 2×100 ml aliquots of distilled water. Next the organic phase was dried over magnesium sulfate and decolorized using activated charcoal. Passage of the solution over a bed of basic aluminum oxide removed all solids and trace colored impurities. The bulk solvent was removed via rotary evaporation at 50°–60° C. and ambient and reduced pressures. The tripropargyl ether was recovered as a light yellow solid (m.p. 73.3° C.) at a yield of greater than 80%.

EXAMPLE 3

Preparation of Dipropargyl Ether of 2-Phenyl Hydroquinone

To a 1000 ml triple necked round bottom flask fitted with a mechanical stirrer, $N_2$ inlet and outlet adapters, liquid addition funnel and a re-circulating water bath were added 500 ml of 20% (wt) aqueous sodium hydroxide solution, followed by 6.0 grams of tetrabutylammonium bromide (0.019 moles). Afterwards, with stirring, the reaction vessel was vigorously purged with $N_2$ while equilibrating to 30° C. (re-circulating water bath temperature). To the aqueous solution was then added, in one portion, 100.0 grams (0.54 moles) of 2-phenyl hydroquinone. Immediately the addition funnel was charged with 100.0 grams of propargyl chloride (1.34 moles) and addition initiated at a drop-wise rate over the next 2 hours. The reaction mixture was maintained at 30° C. for the next 6 hours and at ambient temperature overnight.

The next morning, the dark organic residue was separated and extracted repeatedly with hot hexane. After combination and concentration of the hexane extractions, the orange liquid residue was dissolved into 300 ml of tert-butyl methyl ether and washed with 2×50 ml aliquots of 5% (wt) aqueous sodium hydroxide, followed by 2×50 ml aliquots of distilled water. The solution was then dried over magnesium sulfate and decolorized with a small volume of activated charcoal. Solids were removed by passage over a bed of basic aluminum oxide, and solvent removed via rotary evaporation at 50°–60° C. at ambient and reduced pressures (<0.5 torr). The light orange, liquid dipropargyl ether was isolated in greater than 80% yield.

EXAMPLE 4

Preparation of a Representative Propargyl Based Underfill

A propargyl based underfill is prepared by mixing the following reagents as described below:

(1) Add the desired amount of transition metal catalyst to the liquid propargyl monomer-containing resin. Heating at low temperature (e.g., 40°–60° C.) may be used to accelerate dissolution of the catalyst. Typically, heating at ~50° C. for ~30 minutes is sufficient to dissolve most catalysts. Alternatively, allowing the monomer/catalyst mix to jar roll overnight is the preferred, albeit slower, method.

(2) Add the activator to the monomer/catalyst mix. Heating monomer in the presence of both catalyst and activator is to be avoided. Hence, simple mixing (stirring or jar rolling) for 1 to 3 hours is preferred.

(3) The desired mass of filler is then added to the resin/catalyst/activator mix. Typical fillers are spherical amorphous synthetic glasses in the size range of 1 to 50 micrometers.

(4) The resulting paste is then degassed using a mixing apparatus capable of mixing under full mechanical vacuum (<0.5 torr).

Thus, a formulation according to the invention was prepared following the above-described procedure. The fomulation contained:

65 wt % of a borosilicate filler (4000E CP2, obtained from Potters Corporation), 35 wt % of the propargyl ether prepared as described in Example 3, wherein the propargyl ether contains:

3000 ppm $(Ni)AcAc)_2$, and 5 wt % (based on organic phase) of triphenyl phosphine.

Analysis of the uncured formulation by differential scanning calorimetry (at 10° C./min) indicated an exotherm maxima at 102° C., and liberated about 425 Joules/gm of paste. Thermal stability of the uncured formulation, as measured by thermogravimetric analysis (at 10° C./min with $N_2$ purge), indicated less than 0.1% weight loss up to 250° C., with decomposition onset at about 325° C.

The formulation was then cured at 150° C. for 10 minutes and analyzed. Analysis on a thermomechanical analyzer (DuPont 943) at 5° C./min gave an $\alpha_1$ of 21.83 ppm/°C., an $\alpha_2$ of 80.8 ppm/°C., and a $T_g$ of 136° C.

While the invention has been described in detail with reference to certain preferred embodiments thereof, it will be understood that modifications and variations are within the spirit and scope of that which is described and claimed.

That which is claimed is:

1. A composition useful for protecting a solder interconnection between a semiconductor device and a supporting substrate, said composition comprising:

in the range of about 20 up to 80 wt % of a curable thermosetting propargyl ether-based binder system, wherein said binder system has a viscosity at room temperature of no greater than about 2,500 centipoise, and wherein said binder system comprises:

in the range of about 50 up to about 5000 parts per million, on a metals basis, of a transition metal curing catalyst, and in the range of about 0.1 up to about 10 wt % of an accelerator, based on the total weight of the binder system, and in the range of about 20 up to 80 wt % of a filler having a maximum particle size of about 50 microns, wherein wt % is based on the total weight of the composition unless otherwise indicated.

2. A composition according to claim 1 further comprising one or more of a coupling agent, a thixotrope, a dye, an anti-oxidant, a surfactant, an inert diluent, a reactive diluent, a fluxing agent or an anti-bleed agent.

3. A composition according to claim 1 wherein said propargyl ether-based binder system comprises one or more additional monomers selected from the group consisting of vinyl ethers, divinyl ethers, diallyl ethers, monomaleimides, and bismaleimides.

4. A composition according to claim 1 wherein the propargyl ether component of said propargyl ether-based binder system comprises a propargyl ether compound having structure I as follows:

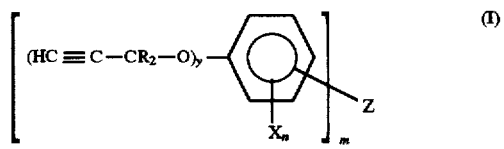

wherein:

X is selected from alkyl, cycloalkyl, alkenyl, alkynyl, aryl, alkoxy, halogen or cyano;

Z, when present, is a di- or trivalent radical capable of linking two or three of the propargyl moieties;

each R is independently selected from hydrogen or alkyl having up to 40 carbon atoms;

m is 1, 2 or 3; and n is an integer from 0 up to 3; and y is an integer from 1 up to 3.

5. A composition according to claim 4 wherein X, when present, is selected from alkyl, alkenyl or aryl.

6. A composition according to claim 4 wherein Z, when present, is selected from:

—O—,

—C(O)—,

—C(O)—O—,

—O—C(O)—O—,

—S—,

—S(O)$_2$—,

—[CR'$_2$]$_x$—, wherein each R' is independently selected from hydrogen, alkyl, fluoroalkyl, cycloalkyl, fluorocycloalkyl or aryl, and x is an integer falling in the range of 1 up to 20, —[O—(CR'$_2$)$_{x'}$]$_y$—O—, wherein each R' is independently as defined above, x' is an integer falling in the range of 1 up to 6, and y is an integer falling in the range of 1 up to 20, —SiR'$_2$—, wherein each R' is independently as defined above, —SiR'$_2$—[—O—SiR'$_2$—]$_{y'}$—, wherein each R' is independently as defined above, and wherein y' is an integer falling in the range of 1 up to 20, —NR'—, wherein each R' in independently as defined above, $$-\underset{|}{N}-,$$

arylene, alkylene-arylene, arylene-alkylene, cycloalkylene, or bicycloalkylene.

7. A composition according to claim 4 wherein R is selected from hydrogen or methyl.

8. A composition according to claim 4 wherein m is 2; and n is an integer from 0 up to 2.

9. A composition according to claim 4 wherein said propargyl ether compound is defined as follows:

Z is —CH(CH$_3$)—, each R is hydrogen, m is 2, n is 0, and y is 1.

10. A composition according to claim 4 wherein said propargyl ether compound is defined as follows:

Z is $$-\underset{|}{C(CH_3)}-,$$

each R is hydrogen, m is 3, n is 0, and y is 1.

11. A composition according to claim 4 wherein said propargyl ether compound is defined as follows:

X is phenyl,

Z is not present, each R is hydrogen, m is 0, n is 1, and y is 2.

12. A composition according to claim 11 wherein said propargyl ether compound is a derivative of hydroquinone.

13. A composition according to claim 11 wherein said propargyl ether compound is a derivative of resorcinol.

14. A composition according to claim 4 wherein said propargyl ether compound is defined as follows:

Z is —C(CF$_3$)$_2$—, each R is hydrogen, m is 2, n is 0, and y is 1.

15. A composition according to claim 1 wherein the viscosity of said composition at room temperature falls in the range of about 3,000 up to about 150,000 centipoise.

16. A composition according to claim 1 wherein the viscosity of said composition at a working temperature of up to about 100° C. is no greater than about 3,000 centipoise.

17. A composition according to claim 1 wherein the majority of said filler particles are spherical, and wherein said filler has a low coefficient of thermal expansion, is non-conductive, and has low levels of extractable ions.

18. A composition according to claim 1 wherein said filler has an emission rate of less than about 0.01 alpha particles/cm$^2$-hr.

19. A composition according to claim 1 wherein the particle size of said filler falls in the range of about 0.5 up to about 20 micrometers.

20. A composition according to claim 1 wherein said filler is selected from alumina, aluminum nitride, boron nitride, borosilicate glass, diamond dust, silica, quartz, silicon, silicon carbide, titania or zirconium tungstate, optionally treated with coupling agents and/or lubricants.

21. A method of protecting a solder interconnection between a semiconductor device and a supporting substrate, said method comprising:

attaching said device to said substrate by a plurality of solder connections that extend from the supporting substrate to electrodes on said semiconductor device, thereby forming a gap between said supporting substrate and said semiconductor device, filling said gap with a composition according to claim 1, and subjecting said composition to curing conditions.

22. A method according to claim 21 wherein said substrate is an organic or an inorganic material.

23. A method according to claim 22 wherein said organic substrate is a laminate.

24. A method according to claim 22 wherein said inorganic substrate is a silicon support, a ceramic support, sapphire or porcelain coated on steel.

25. A method according to claim 21 wherein said curing conditions comprise subjecting said composition to a temperature of up to about 170° C. for up to about 2 hours.

* * * * *